United States Patent
Moliere et al.

(10) Patent No.: US 9,046,221 B2
(45) Date of Patent: Jun. 2, 2015

(54) PROCESS TO CREATE A COLLISION BETWEEN A STREAM OF GAS AND PARTICLES AND A TARGET

(71) Applicant: General Electric Company, Schenectady, NY (US)

(72) Inventors: Michel Moliere, Belfort (FR); Christophe Verdy, Evette-Salbert (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 541 days.

(21) Appl. No.: 13/719,876

(22) Filed: Dec. 19, 2012

(65) Prior Publication Data

US 2013/0306154 A1   Nov. 21, 2013

(51) Int. Cl.
- F23N 1/02 (2006.01)
- F17D 3/00 (2006.01)
- G01N 25/02 (2006.01)
- G01N 33/22 (2006.01)
- G01N 25/00 (2006.01)

(52) U.S. Cl.
CPC ...... F17D 3/00 (2013.01); G01N 25/00 (2013.01); G01N 25/02 (2013.01); G01N 33/22 (2013.01)

(58) Field of Classification Search
CPC .................................................. G01N 25/00
USPC .............................................................. 431/12
See application file for complete search history.

(56) References Cited

U.S. PATENT DOCUMENTS 5,120,582 A * 6/1992 Browning .................. 427/446

FOREIGN PATENT DOCUMENTS

DE    10 2010 045 598 A1    3/2012

OTHER PUBLICATIONS

Seiersten et al., Werkstoffe and Korrosion 38, 532-540 (1987).*
French Search Report and Written Opinion dated Oct. 23, 2012 FR1254558.
Marion Seiersten et al: Sodium vanadate induced corrosion of McrAly coatings—Burner rig studies, Materials and corrosion/ Werkstoffe Und Korrosion, vol. 38, No. 9, Sep. 1, 1987.
Lyyranen J et al: Corrosion studies with a new laboratory-scale system simulating large-scale diesel engines operating with residual fuels, Fuel Processing Technology, Elsevier BV, NL, vol. 86, No. 4. Jan. 25, 2005.

(Continued)

Primary Examiner — Kenneth Rinehart
Assistant Examiner — Gajanan M Prabhu
(74) Attorney, Agent, or Firm — Dority & Manning, PA

(57) ABSTRACT

A process to create a collision in controlled conditions between a stream of gas and particles and a target includes the generation of a stream of gas and particles, of given composition, in the form of a unidirectional beam, using a supersonic burner comprising a combustion chamber and a gas gun, the combustion chamber being fed with a set of fluids comprising a set of gases comprising an oxidizer, and a specific liquid fuel. The generation of a collision between the beam and the target includes the adjustment of the fuel flow, the flow of each gas and the adjustment of the distance between the burner and the target, so as to obtain at the impact point the desired values of the following parameters: (i) the gas temperature or the temperature of the target, and (ii) the gas speed.

8 Claims, 1 Drawing Sheet

(56) References Cited

OTHER PUBLICATIONS

Dennis S. Fox et al., Sea Salt Hot Corrosion and Strength of an Yttria-Containing Silicon Nitride, Journal of the American Ceramic Society, vol. 80, No. 11, Nov. 1, 1997.

Allen L. Robinson et al., Experimental Measurements of the Thermal Conductivity of Ash Deposit: Part 2. Effects of Sintering and Deposit Microstructure, Energy & Fuels, American Chemical Society, Washington DC, US, vol. 15 No. 1, Jan. 1, 2001.

* cited by examiner

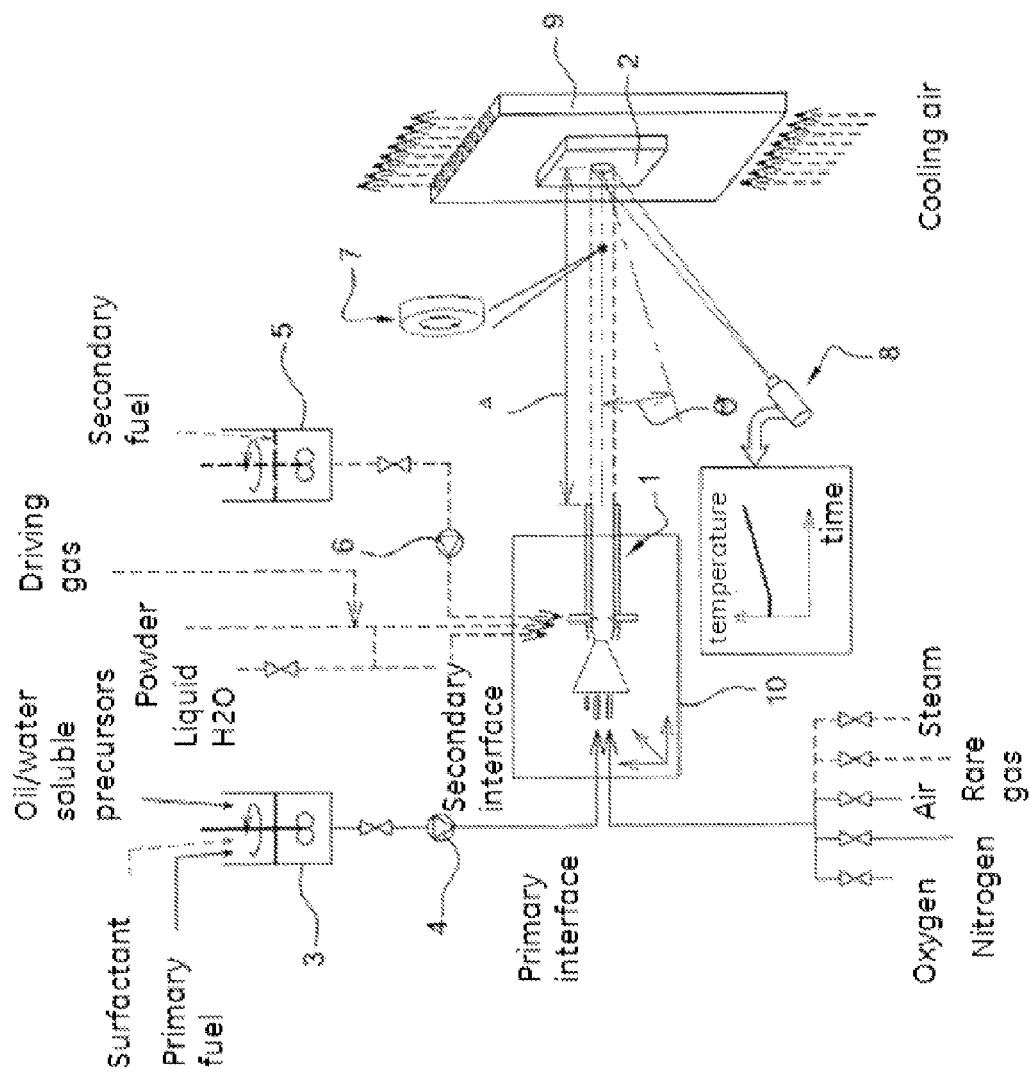

PROCESS TO CREATE A COLLISION BETWEEN A STREAM OF GAS AND PARTICLES AND A TARGET

FIELD OF THE INVENTION

The present invention generally involves a process to create a collision in controlled conditions between a stream of gas and particles and a target. It concerns in particular all processes which result from the meeting between, on the one hand, a stream of gas and particles that features high temperature and high speed, and that will be designated by the simple term of "stream," and on the other hand, a fixed or mobile material object which one will call "hot part" or "target." This meeting between the stream and the target will be called "collision" and the resulting processes will be designated by the collective term of "interaction(s)" between the stream and the target (or the hot part).

BACKGROUND OF THE INVENTION

In the transport and energy sectors, many thermal equipment items include hot parts. There are for example boilers, ovens, blast furnaces, stationary gas turbines, jet engines, turbochargers, or internal combustion engines. The "hot path" of this equipment is defined as the set of volumes and pipes in which the stream of gas and particles flows. As the lifetime and the performances of the hot parts strongly depend on their interactions with the stream, it is important to be able to predict these interactions as accurately as possible.

Ash particles have three possible origins. They can come from a fuel containing various foreign elements which will be designated by the term "contaminants," namely: alkali, alkaline-earths or transition metals; sulfur; aluminum; silicon; chlorine; phosphorus; mercury; etc. These "contaminated" fuels, of fossil or biogenic origin, can be solids (coal; lignite; wood; straw; peat; domestic residue; etc.), liquids (contaminated petroleum distillates; heavy fuels; HCO; LCO; oil residues; raw vegetable oils; alcohols; bagasse; biodiesel; etc.) or gases (synthesis gas or "syngas;" blast furnace or coke-oven gas; biogas; etc.). Ash can also come from the combustion air: for example, jet engines are fed with fuels of high purity (kerosene; jet fuel) but they ingest substantial quantities of contaminants contained in the atmosphere, such as sea salts or dust, in particular particles of "CMAS" ("calcium magnesium aluminosilicates"), which undergo some transformations while crossing the flames. Finally, they can come from "ash modifying agents" or "ash modifiers," that is to say substances that are introduced intentionally into the combustion systems to inhibit the corrosion of the hot parts or to modify the nature and the properties of the inorganic phases formed in the flames.

Whatever their origin, there are three steps in the fate of ash particles: a step of generation or transformation in the flame; a step of transport within combustion gases; possibly one or more shock(s) with machine components. After the step of generation or transformation, the ash particles are in more or less stable suspension within the stream of combustion gases ("carrier gas") and cross the hot path (step of transport) in a solid, liquid, or partially liquid/solid state, according to the local thermal conditions.

One is then in the presence of a dual stream. One stream is a gas stream which forms, according to the terminology of fluid dynamics, a "stream tube" and which is described by four main parameters: geometrically by its "section" which is the cross-section of the stream tube, kinematically by a speed field, thermally by a temperature field, and chemically by its composition ($O_2$; $CO_2$; $H_2O$; $SO_2$ etc.). The other stream is a particles stream that moves in this same "stream tube" and has the same speed, temperature, and cross-section as the gas stream, and is also defined by the concentrations of the phases contained in the particles.

The collision between this dual stream and a target generates, from the point of view of the stream, multiple kinematic effects: deviation of the gas trajectory with the creation of eddies; rebounds of certain particles on the target with changes of their trajectories; "capture" of some particles by the target, possibly followed by their expulsion by other particles. It also generates complex physicochemical "interactions" between the stream of gas and particles and the target, which cover in particular: matter transfers (formation of deposits or scratching-out of material from the target); heat transfers (by forced convection); mechanical effects (shocks undergone by the part); chemical interaction (possible reactions between the target wall and the particles and/or gases: oxidation; sulfidation; etc.); metallurgical effects (superficial hardening of the target; phase changes in the thermally affected zone, etc.). These interactions determine the main three "modes of degradation," which the material of the target can undergo, namely: erosion; fouling; and corrosion.

Erosion is a physical degradation of the material surface caused by high impact speeds and some hardness of the particles; it affects the lifetime of the hot parts. Fouling is a form of reversible or irreversible degradation of the surface cleanliness of the material which results from the formation of notable quantities of deposits having properties of adhesion to the target and/or aggregation and internal cohesion. Fouling has a negative impact on the aerothermodynamics performances of the hot parts and, when it is irreversible, on their lifetime. In the following, the term "deposition" will be used to indicate the formation process of a deposit. One can define the "deposition rate" on a portion of surface of the target as the mass of particles which settles on it, divided by the time and the surface area. It is noteworthy that, when the particles are in the liquid or in a pasty state, i.e., are at a temperature higher than their solidus, their deposition rates are much higher than the same particles taken in the solid state. Moreover, an initial process of fouling consisting of the deposition of an ash film can be followed by the formation of an additional corrosion film (by hydrated iron oxides, for example).

In the third damaging mode which is corrosion, the degradation of material results from a chemical and/or electrochemical attack by the particles and/or the gas. The lifetime of the hot parts is also impacted by corrosion. For corrosion caused by ash, it is necessary that either corrosion starts from a previously formed deposit, which can be very thin, not visually detectable and not fouling, or corrosion is coupled with erosion (effect of "erosion-corrosion"). Consequently, it is rational to distinguish on the one hand two modes of "primary interactions" which are erosion and deposition, and on the other hand a mode of "secondary interaction"—corrosion—which can be associated with one or the other of the primary interactions.

As a consequence of the very fast kinetics of electrochemical attacks in molten electrolytes, a molten phase will cause corrosion with much higher severity than a solid phase. Two modes of degradation can combine and have harmful synergistic effects as in the case of erosion-corrosion and corrosion under deposit. In stationary or aircraft gas turbines, the three modes of degradation can be encountered in a differentiated manner according to the conditions. For example, particles of CMAS in the molten form (high temperature) will tend to foul then to corrode, while the same particles present in the solid state will rather tend to erode the hot parts. One will thus note the complexity resulting from such combinations between the modes of interaction. Therefore, to define sure strategies of prevention or reduction of these effects, it is required for expensive installations, or for equipment subject to drastic safety regulations (stationary gas turbines; jet engines), it is necessary to resort to experimentation to reproduce the feared mode(s) of degradation. Such experimentation must be representative of the target and the stream of gas and particles. Now, it is certainly easy to reproduce the properties of the target that influence the step of interaction. These properties are primarily its geometry, the chemical composition and the metallurgical structure of the material, its mechanical and thermal properties, and its surface quality which can result from a mechanical treatment (polishing, sand-blasting, shot-peening, etc.) or from a metallic, ceramic or "cermet" type coating. On another hand, it is more difficult to reproduce a "representative stream," i.e., to reproduce all the characteristics of the gas stream and especially those of the particle stream intervening in the step of interaction. These characteristics are (i) for the gas stream: the temperature and speed fields, the degree of turbulence, the gas composition; and (ii) for the particles stream: the kinematic characteristics (with speeds being identical to those of gas); geometrical properties (sizes); thermal properties with temperatures being identical to those of gases; coefficient of expansion; conductibility; mechanic properties (hardness; elasticity modulus; impact resistance); physical characteristics (melting point; crystallize, amorphous or vitreous state; porosity; rheology in the case of liquids) and chemical properties (reactivity with respect to the material of the target). It is clear that most of these characteristics cannot be reproduced without re-creating the actual source of particles.

It is appropriate moreover that one also controls the duration of the collision and the local collision conditions, i.e., the conditions which prevail at the very point of impact and which include geometric conditions such as the angle of incidence; aero-thermal conditions such as the speed and temperature of gas and particles; the skin temperature of the target which depends not only on the gas temperature but also on the thermal losses of the target as it will be specified below.

One will speak about "collision in controlled conditions" when all the above mentioned conditions are controlled. However, a review of prior art on the subject shows that the existing processes and experimentation devices do not meet these criteria of representativeness or suffer from shortfalls or major drawbacks. A first traditional experimental method consists of maintaining a target within a "bed" of real or synthetic ash powder, for a defined duration, under a controlled atmosphere. This method, which often is called "immersion test," proceeds in isothermal conditions. It is primarily static, because, even if the atmosphere can be put in circulation, the sample is not exposed to a stream of particles but is immersed in a bed of static particles and is not in direct contact with the gas.

A second traditional method, often called a "thermo balance test," consists of forming an initial deposit of ash on the target, for example by spraying a fog of a solution of the "precursors" and then passing it in a flame. The term "precursors" designates substances which generate, at high temperature, the particles and possibly certain components of the gas stream such as $SO_2$. The target is then introduced into a thermo balance within which the temperature and the composition of the atmosphere are controlled. One can thus monitor, in isothermal conditions, the ash/material interaction by thermo-gravimetric analysis. However, the interaction between the particles and the target are also static here since the deposit preexists when the test starts. In fact, because of the design and the risks of fouling/corroding the "noble" components of the thermo balance, one cannot make particles circulate in it during the test.

Consequently, both the "immersion test" and "thermo balance test" are primarily static in nature and reproduce neither the process of continuous generation of a deposit, nor the velocity of particles.

A third method relies on the use of "burner rigs" which are mainly intended to study corrosion at high temperature. According to a typical design of a burner rig, several probes of the target are placed in an isothermal oven which is swept by the combustion gas stream produced by a burner. To generate the stream of ash particles, one installs, in the burner/oven connection duct, an injector that is fed with an aqueous solution containing the desired precursors. One can extract at defined dates the coupons from the oven, quantify the deposits formed thereon, and subject them to chemical, metallographic, and mechanical tests.

These traditional burner rigs suffer from several limitations and disadvantages. A first major disadvantage lies in the basically static character of these tests and the impossibility of imposing any important and fast temperature variation due to the strong thermal inertia of the rig which is necessary for obtaining a good temperature control. A second disadvantage lies in the relatively low speed range (from a few cm/s to a few m/s) that one can create in it in an economic way due to the non-negligible sections of the various elements of the hot path (conducts and oven). Let us consider for example, a miniaturized burner rig in which the oven would have a section of passage of only 10×10 cm (hardly allowing the handling of the probes). A simple calculation shows that it would be necessary, to obtain a temperature of 850° C. and a speed of 300 m/s, to generate a combustion gas flow of approximately 10,000 $m^3$/h and to burn approximately 130 l/h of fuel (kerosene or diesel fuel). Moreover, the strong pressure drop caused by this high speed would require using an air compressor to feed the burner and a design of the hot path acceptable at the temperature and the pressure (tightness constraints). The generation of high speeds would thus induce elevated investment and operation costs. A third disadvantage is related to the poor definition of the stream lines of the gas and particles inside the oven, precisely because of the limited speeds, with a risk of stratification or even segregation of the particles at the bottom of the oven by gravity effect. A fourth disadvantage lies in the possible chemical interferences between certain anions and cations in the aqueous solution to be sprayed. For instance, one cannot mix calcium or barium ions with sulfate ions which are used as $SO_2$ precursors. Finally, a fifth disadvantage lies in the existence of "memory effects." During a given test "E," one of the injected precursors (e.g., X) can partially be retained on the walls of the hot path (by deposition, adsorption, or absorption) and be then released during a later test "E+n" especially if this test is carried out at higher temperature and speed. Such "a memory effect" that tends to distort both test "E" (defect of X) and test "E+n" (undesirable presence of X) is also insidious as it is detected only during the test "E+n." Such effects are encountered for example with chromium oxide or boron oxide. The closer to the oven the precursors are injected, the less they are likely to be partially retained. One can thus inject the solution in a point close to the entry of the oven containing the probes. However this does not suppress the risk of retention on the walls of the oven. As this effect affects insulating materials both at their surface and in their bulk, the only way of removing this risk is to frequently change these insulating materials, which results in a costly and tedious procedure when one wishes to carry out programs comprising a significant number of tests with very different ash compositions.

Consequently, the existing methods either do not make it possible to create streams representative of gas and particles at high temperature and high speed, or present major drawbacks. It will be noted that these three methods rely on two common designs points. First, the gas stream is entirely confined in a tight and isothermal set of conduct and oven. Second, the target is entirely contained in this oven and is thus exposed to rigorously isothermal conditions in all its points. These design points aim at creating isothermal and uniform conditions of interaction for the target, conditions which are regarded as essential in order to obtain sufficiently repeatable and reproducible results.

The present invention aims at remedying these disadvantages of the existing processes, in particular those related to the thermal inertia.

BRIEF DESCRIPTION OF THE INVENTION

Aspects and advantages of the invention are set forth below in the following description, or may be obvious from the description, or may be learned through practice of the invention.

A purpose of this invention is a process to create a collision in controlled conditions between a stream of gas and particles and a target. In the process according to the invention, the collision is implemented according to desired values, defined at the point of impact between the stream and the target, of the following parameters: (i) the gas temperature or the target temperature, and (ii) the gas speed.

The process includes the generation of a stream of gas and particles, of given composition, in the form of a unidirectional beam, using a supersonic burner including a combustion chamber and a gas gun. The combustion chamber is fed on the one hand with fluids that include gases that include an oxidizer, and on the other hand a liquid fuel composition that provides after combustion the given composition of gas and particles. The liquid fuel includes, as particle generation agents, hetero-molecules in the oil soluble form or in the water-soluble, emulsified form, and, as gas generations agents, some hetero-elements selected among S, P, and halogens. The process includes the generation of a collision between the beam and the target, the angle of incidence of the beam on the target being adjusted at a given value. The process further includes fuel flow control, the flow of each gas, and the adjustment of the distance between the burner and the target, so as to obtain at the point of impact the desired values of the following parameters: (i) the gas temperature or the target temperature, and (ii) the gas speed.

Thus, the combined use of the supersonic burner, the specific liquid fuel including specific hetero-elements, and the specific adjustment of the fuel flow of each gas and of the distance between the burner and the target, make it possible to create, in a fast and simplified way, collisions in controlled conditions, and make it possible in an advantageous way to vary quickly and strongly the temperature at the impact point, which is not possible in the existing processes. One can thus carry out dynamic tests, and no longer only static ones.

The gas can include air or one or more gaseous diluents chosen among nitrogen, carbonic gas, and rare gases. The gas can include one or more gases chosen among sulfur dioxide and the halogens.

The burner can be moreover fed, downstream from the combustion chamber, with a compound chosen among the following compounds: a fuel, called "secondary fuel;" liquid water; particles called "secondary particles."

During the collision, a relative movement can be created between the target and the beam, this movement being a translation, a rotation, or a combination of both.

The process can include a step of monitoring the temperature of the target at the impact point versus time in order to characterize the nature of the particle/target interaction.

According to a mode of realization of this process, a constant temperature over the test duration denotes the absence of ash deposition, an increase in the temperature denotes a deposition of ash, and an evolution of temperature showing an increase interrupted by large drops denotes a deposition of particles stopped by phenomena of cracking or scaling.

The process may include the exposure of the target to a collision in controlled conditions with a flow of secondary particles.

The purpose of the invention may also be the use of the process described above to simulate and characterize the physicochemical interactions between the target and the stream of gas and particles.

The process may also be used to simulate and characterize a process of erosion, adhesion, or corrosion.

Those of ordinary skill in the art will better appreciate the features and aspects of such embodiments, and others, upon review of the specification.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which:

FIG. 1 is a simplified block diagram of one embodiment of the present invention.

DETAILED DESCRIPTION OF THE INVENTION

Reference will now be made in detail to present embodiments of the invention, one or more examples of which are illustrated in the accompanying drawings. Like or similar designations in the drawings and description have been used to refer to like or similar parts of the invention. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the appended claims and their equivalents.

The applicant has developed a process to generate a stream of gas and particles at high temperature and high speed ("the stream"), for example with a gas temperature ranging between 600 and 1,800° C. and a gas speed ranging between 100 and 600 m/s, and to create a "collision in controlled conditions" between this stream and a target. This process relies on three design points that strongly differ from those implemented in the previous art. On the one hand, one creates a "stream tube" of gas at high speed and of low section by burning a liquid fuel in a "supersonic burner" and, on the other hand, one generates particles within this gas stream by doping the same liquid fuel with a set of precursor additive, having well defined nature and concentrations. One thus generates a unidirectional stream of gas and particles at high temperature and high speed, whose characteristics are controlled, which, as it is ejected from the burner at high speed, does not require guide-walls and whose temperature gradually decreases along its trajectory.

The target is positioned, in open air, on the trajectory of the beam, in controlled conditions of collision with it, in particular at a given distance and with a given orientation. The "collision in controlled conditions" is voluntarily limited to a zone of small area which is the "zone of impact" of the beam onto the target. This zone is thus the seat of a two processes: (i) an aero thermal interaction with the stream; and (ii) a thermal dissipation, mainly by radiation, towards the ambient conditions, processes that fix the stationary conditions on the impact zone, under constant conditions of collision.

During the development of this process, the applicant has observed, as a remarkable fact, that the stream/target collisions are not subject to any stratification of particles, can be repeated and reproduced in terms of deposition, this although the collision affects only a portion of the target and, taken as a whole, is not isothermal. In terms of terminology, for such streams of gas and particles at high speed, which are primarily unidirectional, one will speak about "beams of gas and particles" or simply "beams."

The applicant has established that this process is free from the limitations inherent to the existing methods. Thanks to the close control of the beam geometry, whose well defined direction and section ensure a precise definition of the impact zone, and thanks to the absence of stratification of the particles in it, the mass flows of particles that impact the target can be reproduced in a much more quantitative and rigorous way that in a burner rig. It is also free from "memory effects" because of the absence of guide walls. After the tests, the applicant has observed the virtual absence of deposits on the internal walls of the burners used. In the rare cases where such deposits are formed, they are detected through an increase of the injection pressure of the fluids, contrary to what occurs in the conducts used in the prior art. Finally, the supersonic burners can, considering their low dimensions (about 10 cm length; 3 cm diameter for the combustion chamber), be easily dismounted, internally washed, with a simple brush, then re-installed, the complete operation lasting hardly a few minutes. It makes it possible to reach speeds of several hundred meters per second, with modest consumptions of fluids, this thanks to the low section of the beam. It enables a very vast range of compositions of gases and particles, thanks in particular to the numerous series of the possible precursors, that the applicant has established. Finally, it makes it possible to control and easily modify the conditions of the collision during the test and thus lends itself to fast changes of thermal and geometrical conditions.

A device according to the invention (or "device") has been designed to implement the three design points set out above. As illustrated on FIG. 1, it includes a supersonic burner 1, several feeds of the aforesaid burner, which, as described in the following paragraph, enable introducing into it a very complete set of liquid fuels, oxidizers, diluents, and precursors in order to create a very broad range of compositions of the beam of gas and particles, a target 2 equipped with a fixation and possibly a cooling device, and metrological means (temperature, pressure, and possibly speed).

In an optional way, the part of the "device" constituted by the supersonic burner 1 and target 2 is installed in a soundproof cabin and is equipped with a system of collection of the combustion gas and of filtration of the particles emitted. The detailed presentation of the process according to the invention is based on FIG. 1 and breaks out into the generation of the stream of gas and particles, the control of the conditions of the stream/target collision, and the application in the study of the stream/target interactions.

A—Generation of the Stream of Gas and Particles

In this document, a supersonic burner means a burner that generates combustion gas at supersonic speed and includes: a combustion chamber equipped with an ignition device (such as a spark plug), which, to reach supersonic conditions, operates under pressure and is fed, in addition to a liquid fuel, with a oxidizing mixture including pure oxygen; a linear portion, preferably dismountable, which will be referred to as "the gas gun" of the burner, which is generally separated from the combustion chamber by a convergent-divergent device and which ensures the development of the high speed flow of the combustion gas; and an orifice of ejection or "outlet orifice" of the combustion gas which is the end of the gas gun.

A kind of supersonic burner is represented by "HVOF guns" (High Velocity Oxy-Fuel) that are fed with liquid fuel. These commercial burners have low sizes, are dismountable, and have in general their walls water-cooled through a double envelope.

The device according to the invention comprises a supersonic burner fed with various fluids gathered in a "primary feeding interface" and a "secondary feeding interface." The "primary feeding interface" located at the inlet of the combustion chamber allows the injection of the following fluids: one or more oxidizing gases such as oxygen, air, nitrogen protoxide, these gases being designated hereafter by the collective name of "oxidizer;" one or more gas diluents such as nitrogen, steam, carbon dioxide, a rare gas, these gases being designated hereafter by the collective name of "diluent;" one or more gases referred to as "specific gas," such as sulfur dioxide ($SO_2$); and a liquid fuel or "fuel," qualified "primary fuel."

For the sake of simplicity, the set formed by the oxidizer, the diluent, and the specific gases will be called, in a generic way, the "oxidizer-diluent." The primary fuel, which can comprise one or more component(s), is doped with additive-precursors which, by combustion, will generate: (i) the wanted particles and (ii) some other gaseous combustion products, such as $SO_2$. Each precursor is incorporated in the fuel in a precise quantity, its mass fraction in the fuel being calculated according to the fuel mass flow rate, so that the corresponding combustion product has the wanted concentration in the beam. This calculation procedure will be specified below and illustrated in the examples of realization of the invention. For the sake of simplification, one assumes, although it is not mandatory, that the fuel is free from sulfur and does not generate any $SO_2$; otherwise, it would be necessary to take it into account in the balance of materials. It thus primarily consists of carbon, hydrogen, and possibly oxygen. The injection of the fuel in the burner can be done through an atomization device that generates a fine spray of fuel droplets and renders the combustion very uniform.

The circuits associated with this "primary feeding interface" are the following ones: the system that feeds the burner with the primary fuel, system also qualified as "primary," includes: (i) a "primary tank" 3, which is preferentially stirred, (ii) a "primary injection pump" 4, (iii) a manual or automatic device for adjusting the fuel flow, and (iv) a pressure gauge at the inlet of combustion chamber; the various fuel components are mixed in controlled proportions, continuously or in batch, within the primary tank 3, into which the precursors are also introduced in given concentrations; the system that feeds the burner with the oxidizer and diluent, includes: (i) a pressure storage facility and (ii) lines for the distribution of the various gases mentioned earlier, with manual or automatic flow adjustment devices and indicators of the corresponding pressures at the inlet of combustion chamber.

The "secondary feeding interface" comprises a set of piping's located at the inlet of the "gas gun" of the burner, thus downstream of the combustion chamber. It is intended to inject the following substances: liquid water which enables: (i) adjusting the content of $H_2O$ in the combustion gases, (ii) creating a fast temperature drop and possibly a quenching, the applicant having observed that when liquid water is injected downstream from the combustion chamber, it generates less flame instabilities than if it is injected upstream of it; a "secondary fuel" that will burn inside the "gas gun" of the burner and whose interest is for example to simulate positive thermal shocks or post-combustion effects such as those taking place in a jet engine; and a powder driven by a gas called "carrier gas."

The circuits associated with this secondary feeding interface are the following: a "secondary fuel feeding system" that is identical to or different from the primary fuel and that includes a "secondary tank" 5, a "secondary injection pump" 6 and a manual or automatic device for adjusting the fuel flow; a circuit for feeding liquid water with a manual or automatic device for adjusting its flow; a circuit for feeding powder, with adjustable flow, including for example a hopper equipped with a vibrator and an inlet of "carrier gas" (nitrogen, rare gas) to move this powder.

Such a powder can be either a material of defined composition and particle size such as alumina, silica, an aluminosilicate, a zeolite, graphite, metallic oxides, etc., or a natural or synthetic ash. It can undergo, to obtain the wanted particle size, a crushing followed by a passing over calibrated sieves. There is a multiple interest for injecting such particles—referred to as "secondary particles"—into the beam: the motion of these secondary particles of micrometric sizes, followed by LASER velocimetry can be used to determine the gas stream velocity; like the primary particles, these secondary particles incorporated in the gas beam lend themselves to specific studies of interaction with the target. One can study in particular processes of erosion of the target by these particles or processes of abrasion of deposits being formed or already formed.

It is thus possible to involve in the beam-target interaction some secondary particles that have controlled chemistry, crystallographic, and morphology and that can be complex: for example, particles of aluminosilicates (CMAS), tecto- or phyllosilicates, etc.

To start the burner, one (i) feeds the burner with the primary fuel. The oxidizer and the diluent (for example: $O_2$+air) (ii) ignites the flame and (iii) waits for its stabilization. Then, if required, one can adjust the compositions and/or the flows of fuel or oxidizer-diluent. One can even feed the burner with other fluids (another oxidizer or diluent; specific gas; secondary fuel; water) to obtain the wanted properties of the beam. One will wait again for the flame stabilization.

The precursors or "doping agents" that are introduced into the primary fuel tank are "hetero-molecules," this term designating molecules containing at least one "hetero-element" i.e., an element distinct from C, H, and O. The hetero-elements of these hetero-molecules are selected to reproduce the contaminants, inhibiting elements, or ash modifiers, the presence of which is wanted in the beam. The substances resulting from the transformation of these hetero-elements in the flame will be called "artificial products (of combustion)." They break down in: "artificial, gaseous products" such as $SO_2$ and possibly $P_2O_5$ and $X_2$ (halogens) in the cases of the hetero-elements sulfur, phosphorus, and halogen, respectively; "artificial, non-gaseous products" that will generate the solid particles (e.g.: $Fe_2O_3$, $Al_2O_3$) or liquids (e.g.,: $Mg_3V_2O_8$ above 1170° C.) in the cases of the hetero-elements iron, aluminum, magnesium and vanadium, respectively.

The hetero-molecules used are either oil-soluble, generally organic substances, in which case the stirring of the tank suffices to uniformly mix them with the fuel phase, or water-soluble, generally inorganic substances, brought for example in the form of aqueous solutions, in which case a surfactant is also added to the fuel in order to form a stable and homogeneous emulsion or a micro emulsion of these hetero-molecules in the fuel.

The operations of mixing in the primary tank can be carried out either in discontinuous (or "batch") mode, which corresponds to the case represented in FIG. 1, or in continuous mode and can be manual or automated.

The applicant has established that the list of the oil-soluble and water-soluble precursors that one can incorporate in the primary fuel is extremely wide. A non-exhaustive list is provided below.

Water-soluble precursors: One can in particular use sulfuric acid (as a source of sulfur); metal nitrates or acetates (as sources of sodium; potassium; calcium; magnesium; iron; nickel; aluminum; titanium; zirconium; rare earths; mercury, etc.); metal sulfates (as sources of metals and incidentally of sulfur); ammonium halides, alkaline, and alkaline-earth metal halides (as sources of halogens, alkaline, and alkaline-earth metals); carbonates (as sources of alkaline metals and incidentally of $CO_2$); alkaline hydroxides (as sources of alkaline metals); ammonium phosphate (as a source of phosphorus); boric acid (as a source of boron); and chromic oxide (as a source of chromium). These substances will be associated by taking account of incompatibilities between ions, as already indicated. The surfactant used to generate the emulsions or micro-emulsions of the water-soluble precursors in the fuel phase are those that promote water-in-oil emulsions, i.e., those having low hydrophilic-lipophilic balances ("HLB"). One can take for example a product of the Pluronics® or Brij® series or a polyethoxy-nonylphenol, which substances do not contain any hetero-element.

Oil-soluble precursors: The applicant has determined that one can in particular use carbon bisulfide, thiols, or mercaptans (as sources of sulfur), halogenated hydrocarbons (as sources of halogens), metal carboxylates (as sources of sodium; potassium; calcium; magnesium; iron; aluminum; nickel; lead; bismuth; lanthanides; etc.). The corresponding carboxylic acids can be aliphatic (for example nickel or sodium octoate), naphthenic (vanadyl naphthenate), or aromatic (lanthanum naphtoate). One can also use metal sulfonates (as sources of sodium; potassium; calcium; magnesium; iron; aluminum; nickel; lead; bismuth; yttrium; etc.); metal alkoxydes (as sources of alkaline, alkaline-earth metals or transition metals including: Ti; V; Zr; Y; lanthanides; Bi; Pb); "chelates" such as acetylacetonates (as sources of calcium; magnesium; aluminum; iron; nickel; chromium; manganese; scandium; vanadium; zirconium; yttrium; molybdenum; tungsten etc.); metal carbonyls or metallocenes (as sources of iron, nickel, molybdenum, tungsten); silanes or siloxanes (or "silicone oils") as sources of silicon; organophosphorus compounds or organic phosphonates (as sources of phosphorus); and boranes or organic boric esters (as sources of boron), etc.

For the complete dissolution of these oil-soluble hetero-molecules in the fuel, one can adjust the composition of the fuel. The fuel can thus include the following components: kerosene fractions; petrol ethers (or naphtha) fractions; diesel oil fractions; aliphatic, aromatic or naphthenic hydrocarbons; esters; alcohols; vegetable oils; ethers; glycol ethers, such as the monoethyl ether of the diethyleneglycol (or "carbitol") or the monobutyl ether of the diethyleneglycol (or "butylcarbitol"); methyl esters of vegetable oils ("biodiesels"), etc. One can take for example formulations based on mixtures of alcohols having chains of variable lengths and structures (including methanol, ethanol, or isopropanol) and hydrocarbons of variable PONA indices. One can change their relative proportions in order to adjust the solvency power (related to polarity and "Π bonds" effects) of the resulting phase. One can also incorporate in the fuel some proportions of other organic substances that are fully miscible with the fuel, such as: (i) beta-diketones (e.g., acetylacetone) in consideration of their "chelating" effect on metals; (ii) tetrahydrofurane, known for its powerful solvency power; (iii) dimethyl carbonate, (iv) propylene or ethylene carbonate. It should be noted that such changes in composition of the fuel alters its calorific value and thus tends to change the flame temperature. This effect can be corrected while adjusting the equivalence ratio of the flame or the composition of the set of oxidizer-diluent.

An important advantage of oil-soluble precursors lies in the fact that they cause very little reciprocal incompatibilities, in contrast to the already mentioned precipitation issues faced with aqueous solutions. Another advantage relates to the incorporation of precursors of $SO_2$ that are often present in large concentrations in industrial combustion gases. In the process according to the invention, one can incorporate elevated concentrations of carbon bisulfide or mercaptans because these substances are fully miscible with the fuel and are not corrosive, contrary to sulfuric acid, which is moreover incompatible with the alkaline-earth metals. It will be noted that, instead of incorporating sulfur in the form of a hetero-element in the fuel, one can also inject an adequate flow of $SO_2$, as a "special gas," such injection being made at the oxidizer-diluent feeding interface, in order to reproduce the desired content of $SO_2$ in the beam. This operation is, however, more expensive, and the storage and handling of $SO_2$ cylinders require special precautions.

It is thus possible to reproduce, in nature and concentration, a very complete set of contaminating elements, inhibitors, or ash modifiers for the purpose of the planned studies. For that, one will choose, in the preceding list, hetero-molecules containing these elements and dissolve them in the fuel, in precise concentrations as specified below.

B—Control of the Conditions of the Beam-Target Collision

The combustion gas and the particles generated by the supersonic burner are ejected at high speed from the supersonic burner, whose outlet orifice has generally (but not necessarily) a circular section. In the process according to the invention, one intentionally chooses a value ("$\sigma^*$") of this section which is small and smaller than the target size, in order to create on the latter an impact zone of limited area. By concentrating an important flow of particles on this zone, one can obtain an elevated mass flux (the mass flux being defined as the mass flow dividing by the impact area) and thus intensify, at low cost, the beam-target interaction. This thus allows severing the tests and/or accelerating them. One will take for example a diameter $d^*$ ranging between 8 and 14 mm, corresponding to a section "$\sigma^*$" comprised between 0.5 and 1.5 $cm^2$ approximately.

Once ejected from the supersonic burner, the beam remains virtually insensitive to gravity over a certain length, thanks to its high velocity, its unidirectional character (which it has acquired when passing along the linear gas gun), and the absence of frictions on guiding walls. Along this portion of linear trajectory, it cools gradually as it radiates towards the ambient and tends to slightly widen, with a weak opening angle "$\alpha$," which results in a light, progressive increase of its cross-section. The applicant has observed that this angle depends very little on the gas flow and is relatively reproducible for a given burner geometry. For instance, the angle may be 5.5 degrees for a gas gun of 10 mm in diameter.

Let $\delta$ be the distance between the target and the outlet orifice of the burner. One can predict with a rather good precision the diameter ("d") of the beam cross-section at a point located at the distance $\delta$ from the burner using the parameters $\delta$ and $d^*$ (the burner outlet orifice diameter):

$$d = d^* + 2\delta \tan(\alpha/2) \approx d^* + \alpha\delta \quad (1)$$

The approximation made in this equation is possible because the angle $\alpha$ is small.

One thus obtains a good estimate of the area of the impact zone which is equal to:

$$\sigma = \pi d2/4 \approx \pi(d^* + \alpha\delta)^2/4 \quad (2)$$

The value of $\sigma$ can thus be predicted and changed through the diameter $d^*$ of the burner outlet orifice. It can be also checked while measuring the diameter of the easily perceptible, bright spot that is developed by the beam at its impact on a target located at the distance $\Delta$ or, which is equivalent, the diameter of the light oxidation trace left by the beam after the test.

The diameter $d^*$ of the burner outlet orifice being defined, the "critical" characteristics of the beam, i.e., those that control the conditions of the collision and interaction with the target, are the following:

the gas temperature "Tg" or the skin temperature of the target "Ti";

the gas speed (say "Vg");

the molar fractions of the "artificial, gaseous products," $SO_2$ and possibly $P_2O_5$ and $X_2$ (halogens), which, when they are present, affect the chemical balances; and the mass fluxes, defined at the impact point, of the "artificial, non-gaseous products" that will generate the particles that will impinge the target, in the liquid or solid state.

Now, the following analysis shows that, from its design, the device makes it possible to control these characteristics through the parameters used to adjust of the burner operation, i.e., (i) the molar flow of the fuel ("Qf"); (ii) the molar flows of oxidizers ($O_2$, $N_2O$) and of diluents ($N_2$, $CO_2$, rare gases); and (iii) the molar fractions of the precursors incorporated in the fuel.

Control of the Thermal Parameters:

In addition to the gas temperature Tg (which is also that of the transported particles), there is another very important thermal parameter to characterize the collision and the beam-target interaction, which is the "skin temperature" or the temperature at the very impact point. This temperature "Ti" is different from Tg due to the fact that the target is subjected to other heat exchanges (loss by radiation and possibly an internal cooling).

In the science of combustion, one can control the parameter Tg (i.e., the combustion temperature) by adjusting the equivalence ratio of the flame (i.e., the ratio between the fuel flow and the oxidizer flow) and, if necessary, either by altering the nature of oxidizer (using e.g., $N_2O$ to increase Tg) or by introducing a diluting agent (using e.g., $N_2$ or $CO_2$ to decrease Tg) and by adjusting the diluent flow/fuel flow ratio.

The temperature "Tg" at a given point in the beam, located at the distance $\delta$ from the burner, decreases gradually when $\delta$ increases, its initial value being Tg* for $\delta=0$ (burner outlet). The function Tg($\delta$) can be determined in several ways, preferably in the absence of particles in the beam (i.e., with an undoped primary fuel), in order to prevent that the measurement is not biased by a possible incipient deposit. One can in particular place, in the beam, at the distance δ from the burner outlet, a thermocouple 7 fitted for high temperatures, as represented in FIG. 1, its bulb being preferably protected by a shield to avoid its direct contact with the very hot gas and the oxidation of the thermocouple elements. One will take for example a thermocouple of the S type (platinum/platinum rhodium) allowing reaching 1,650° C. or of the C type (tungsten/tungsten-rhenium) that can attain 2,320° C. Considering the high temperature level, it is advisable to apply the traditional measurement correction related to the radiative losses of the thermocouple bulb.

Within the framework of this invention, the gas temperature Tg can also be measured using a "black body radiator" or "radiator body" 7, which is made of a black, refractory, preferably insulating substance and has for example the shape of a cylinder of a few centimeters height and whose bases have a diameter slightly higher than that of the beam cross section. This radiator body is inserted inside a "support plate" (having a thickness higher than the height of the radiator body), through an also cylindrical opening, which has been bored in the support plate, normally to its wall and whose diameter is slightly larger than that of the radiator. This insertion is made so that the base of the radiator that remains visible (which will have been beforehand finely polished) is tangent to the wall of the "support plate." This support plate is made of a very insulating material (such as cordierite). This insertion being made, the radiator will be positioned in the beam so that its axis is identical to that of the beam. Such a cylindrical "radiator body" then plays the role of a black body which develops, on its polished face that is exposed to the beam, a temperature very close to the temperature of the incident gas, its insertion within the support plate making it possible to minimize the thermal losses by conduction and convection through its sides that are not exposed to the beam and are surrounded by the insulating material of the aforesaid support-plate. This temperature can be deduced from the intensity of the radiation of the radiator body knowing that its emissivity is very close to one. Such a radiator body can be fabricated, for example and according to the aimed temperature level, in carborundon, boron nitride, obsidian or hematite. The measurement of the temperature Tg can be made using an optical pyrometer or a thermal camera, as described below. It will also be advisable to apply the corrections for the radiative losses.

In what follows, A designates the distance between the outlet orifice of the burner and the point of the beam where the gas has the wished temperature Tg. One will thus position the target at this distance from the outlet orifice of the burner.

If one wishes to reproduce, at the impact point, not the temperature Tg but the skin temperature "Ti" of the target, one can substitute the operation of adjustment of the temperature Tg, which has just been described, by an equivalent operation of adjustment of the temperature Ti. This temperature Ti results from the stationary heat exchange between: (i) the gas impinging at temperature Tg, (ii) the target having a floating temperature, and (iii) the ambient. It can be measured using a thermometric device that can be: (i) an optical pyrometer, (ii) a thermal camera 8, or (III) a simple thermocouple whose welding is introduced into a cylindrical notch that has been bored on the back of the target, has just a sufficient diameter, and the bottom of which is close to the center of the impact zone (for example at 2 mm from it). When a thermal camera is used, one orients its line of sight towards the center of the impact zone, preferably in coincidence with the normal to the target or making a small angle with this normal. The camera measures, at a given wavelength, the intensity of the light radiation that this zone sends to it and its software calculates the value of the corresponding skin temperature Ti from the value of the emissivity of the bare metal (defined at the same wavelength) or, if necessary, the emissivity of the ash deposit (by approximation, one can take the emissivity of the main crystallographic phase of the ash). This value of emissivity is introduced as an input into the software of the camera before the beginning of the test. The use of a thermal camera is interesting because its use is simple and nonintrusive, it gives a temperature Ti averaged on the impact surface, and the measurement is very little disturbed by the intense conduction and convection effects which affect the target and the gas film around it.

Control of the Gas Speed "Vg"

The device also makes it possible to vary the gas speed Vg, which is also that of the transported particles. To increase or decrease it all while maintaining Tg constant, one will increase or reduce, respectively, the total flow of the combustion fluids without modifying their proportions in order to vary the molar output of combustion gases "Qg" and if necessary one will vary the section σ of the beam, knowing that one has the following equation:

where Vg is expressed in m/s, Qg in mol/s, σ in m, Tg in K and Vmol, the normal molar volume, is equal to 0.0224 Nm³/s (the letter "N" refers to the "normal conditions": 0° C. and 1 atm).

Qg is calculated from (i) the molar flows of burner "entrants" and (ii) the chemical equation of combustion of the fuel, which provides the molecular balance, as illustrated in the first example of realization.

The section σ of the beam at the point of abscissa Δ can be adjusted by modifying the diameter d* of the burner outlet orifice (i.e. the internal section of the gas gun). In fact, according to equations (2) and (3), one has:

$$V_g = (Q_g V_{mol}/\sigma)(T_g/273) = (Q_g V_{mol} T_g)/[273\pi(d^* + \alpha\Delta)^2] \approx 2.611\ 10^5 Q_g T_g/(d^* + \alpha\Delta)^2 \quad (4)$$

where d* and Δ are in m and $Q_g$, $V_{mol}$, $T_g$, and α are respectively in mol/s, Nm³/mol, K, and radians.

This equation makes it possible to estimate with good accuracy the speed of gas at a given point of the beam trajectory, for a given burner geometry.

In order to modify Qg, one can alter the flows of entrants, and if one does not wish to modify the value of Tg, one shall keep constant the proportion between the molar fractions of different entrants in order to keep constant the temperature of combustion, as that is also illustrated in the first example of realization.

The gas speed in the beam can also be measured using a laser velocimetry device (not represented on FIG. 1) while following particles of adequate size (for example 10 μm) that will be injected via the secondary feeding interface that has been described above.

Adjustment of the Molar Fractions of the Precursors

In the following, the notations "$X_i$" and "$X_i^{mass}$" respectively designate the molar fractions and mass fraction of the hetero-element "i" in the fuel. These data are interrelated by the following equation:

$$X_i^{mass} = (M_i/M_f) X_i \quad (5)$$

where $M_f$ and $M_i$ expressed in kg/mol, respectively designate the molar mass of the fuel and the atomic mass of the hetero-element "i."

The notation "$Y_i$" indicates the molar fraction of the same hetero-element "i" in the stream of gas and particles. $Y_i$ can be expressed in function of the molar fraction of "i" in the fuel using the matter conservation balance of this element, that is to say:

$$Y_i = X_i(Q_f/Q_g) \quad (6)$$

or $$X_i = Y_i(Q_g/Q_f) \quad (7)$$

One is reminded that Qf and Qg designate the molar flow rates of fuel and combustion gas respectively.

The equations (5) and (6) lead to:

$$X_i^{mass} = (M_i/M_f)X_i = (M_i/M_f)Y_i(Q_g/Q_f) \quad (8)$$

Equation (7) equals to:

$$Y_i = X_i^{mass}(M_f/M_i)(Q_f/Q_g) \quad (9)$$

a) Precursors Generating "Artificial, Non-Gaseous Products"

When a hetero-element, for example a metal, is transformed during combustion into an "artificial, non-gaseous product," i.e., into solid or liquid particles, it is appropriate to control the mass flux of this product in the combustion gas. As the chemical nature of the formed particles is not undoubtedly known, one will rather control the mass flux of the hetero-element in the combustion gas. This flux "Fi" which expresses the mass of the element "i" transported per unit of time and surface, writes:

$$F_i = X_i Q_f * M_i/\sigma \quad (10)$$

where Fi is expressed in kg/s/m² and σ designates the cross section (in m²) of the beam at the impact point. Consequently, the molar fraction Xi writes:

$$X_i = F_i \sigma/(Q_f M_{Xi}) \quad (11)$$

The mass fraction in the fuel of the hetero-element "i" acting as a particle generator can been expressed using equation (5):

$$X_i^{mass} = F_i \sigma/(Q_f M_f) \quad (12)$$

b) Precursors Generating "Artificial, Gaseous Products"

When one hetero-element, such as sulfur, phosphorus, a halogen, etc., is transformed during combustion into an "artificial, gaseous product," it is appropriate to control the concentration (for example the molar fraction) of this gaseous product in the combustion gas, because it is this property which determines the chemical equilibriums in the gaseous phase. For instance, the sulfation/desulfation equilibrium of metallic oxides in gases depends on the molar fraction of $SO_2$ in the gas, or, which is equivalent, on the molar fraction of the sulfur hetero-element (say "$Y_S$") in the gas.

Thus, in the case of sulfur, for example, equation (6) gives: $Y_S = X_S (Q_f/Q_g)$. Equations (8) and (9) give, respectively:

$$X_S^{mass} = (0.03206/M_f)Y_S(Q_g/Q_f) \quad (13)$$

$$Y_S = 31.19 X_S^{mass} M_f(Q_f/Q_g) \quad (14)$$

Note: The options of controlling the mass fluxes (Fi) or the molar fractions (Yi) of the various hetero-elements in gases are in fact equivalent. In fact, these two characteristics are interdependent through equations (7) and (10), from which one draws:

$$Y_i = F_i \sigma/(M_f Q_g) \quad (15)$$

This way of controlling the characteristics of the beam will be illustrated in details in the examples of realization of the invention.

In summary, the incorporation into the fuel, according to the invention, of the very wide range precursors identified by the applicant, makes it possible, on the one hand, to reproduce, in composition and in mass fluxes, the stream of particles and, on the other hand, to adjust, in the beam, the concentration of $SO_2$ or another specific gas ($P_2O_5$, halogens).

C—Application to Beam-Target Interaction Studies.

In what follows, it is obvious that to change and fix the relative positions of the target and the burner, one can move the target with respect to the burner or vice versa.

The "test target" (or simply the "target") on which one will generate and characterize the collision consists of a probe that has been machined in the material to be studied, which can be metallic or a ceramic. This probe that has been weighed beforehand is generally flat and thin in thickness. It can have however any other shape and be in particular cylindrical. Its "exposed face," i.e., the portion of its surface put in contact with the hot gas, is contained in (or tangent to) a vertical plane. The roughness of the exposed face which conditions the interaction with the beam (in particular the adhesion and erosion processes) is defined during the machining of this face. One can take for example a "Ra" (arithmetic mean roughness) ranging between 0.01 to 10 μm. It will be noted that the surface quality of the test target can be slightly damaged during the adjustment operations of Tg (or Ti) and Vg, which are performed before the interaction study properly said and imply exposing the probe to the stream of hot gas. In order to avoid such a deterioration, one can use, during these adjustment operations, an "auxiliary target" identical to the test target. However, this operational detail is not essential for the implementation of the invention.

After the adjustment of Tg (or Ti) and Vg, the target will be placed on the trajectory of the beam, preferably in a vertical plan, with the corresponding distance "Δ" from the burner.

To create a collision in controlled conditions between the beam and the target, one will precisely direct the beam of gas and particles towards a predetermined point of the target, preferably its center so that the radial flow of thermal loss around the impact center is uniform to obtain a homogeneous temperature field on the zone of impact. Before and after the collision, one will direct the beam in a "safety direction," for example a metallic grid installed outside the burner-target line.

Within the framework of the invention, one can easily change the collision configuration in playing on the relative geometry configuration of the beam and the target.

For example, one can vary the distance Δ by shifting the target or the burner. Such a shift, if it is fast, makes it possible to simulate fast variations of the gas temperature. To that end, the target (preferably in vertical position) and its support 9 can be installed on a rail, parallel to the beam, on which they can be moved manually or by a motor.

In addition, the beam can be directed in order to form a defined angle of incidence ("θ") with the normal to the target, its axis preferably remaining located in the horizontal plane containing this normal. This orientation can be obtained quickly by a simple rotation of the target around its vertical axis. Having the normal to the target and the beam axis contained in the same horizontal plane makes it possible to install the thermal camera in this same horizontal plane with also a horizontal line of sight. When the angle of incidence θ is zero (the beam axis being perpendicular to the exposed side of the target), the thermal camera cannot be located on this same line and must be off-set, for example by 10 to 45° of angle. The experience shows that this offset does not have a significant effect on the temperature measurement results. Within the framework of the invention, one can thus study, in a specific way, processes of particles adhesion on the target, by selecting an angle θ close to zero for which this effect is maximum or, conversely, one can study the processes of erosion, by selecting an angle θ close to 90° or 30° according to whether the target material is brittle (ceramics) or ductile (metal), any other value of the angle θ being possible for the needs of the study.

Optionally, the burner can be directed in the three directions of space using a remotely controlled multi-axis robot 10 making it possible to carry out the following operations:

varying the angle θ in a discrete or programmed way with, for example, a reciprocating motion between the values (−θm) and (+θm) simulating for example the variation of the incidence angle of combustion gases along the leading edge of a rotating turbine blade; and scanning the target surface with the beam, according to a predefined program, with lateral/vertical translation movements or rotation ones, with for example a constant value of Δ.

Within the framework of the invention, one can also follow the change of the temperature Ti during the test by a manual recording or, better, by adding an acquisition system to the thermometric device in order to obtain a Ti(t) chart that can be recorded or visualized in real time on a screen. The applicant has discovered, as an interesting fact that such a monitoring provides, in the case of a metallic target, simple and precise information about the mode and the evolution of the beam-target interaction. In fact, the following, remarkable points were observed. A temperature Ti remaining constant during the test indicates the absence of deposition, without prejudging the existence of an erosion effect. There can be the formation of a liquid deposit, sufficiently fluid to run out on the wall of the target and not to accumulate at the impact point. This film may be invisible to the naked eye but can be detected at the end of the test using binoculars or a microscope. A temperature Ti increasing during the test indicates on the contrary a process of ash deposition because the thermal conductibility of the deposit being lower than that of the metallic target, the dissipation of heat through the thickness of the target is slowed down. An evolution of Ti showing a regular increase interrupted with fast and strong temperature drops, corresponds to a process of particles deposition that is temporarily stopped by phenomena of cracking or even scaling of the deposit. This kind of evolution that has been discovered by the applicant is due to distinct coefficients of temperature between the target and solid deposit or between various phases of the solid deposit. It is remarkable because it indicates the formation of a "thermally brittle" deposit. One can thus, within the framework of this invention, play on the chemical composition of the particles (ash modifying agents) to try to create or avoid brittle deposits.

In summary, the monitoring of the temperature Ti at the impact point, according to the invention, provides valuable information on the evolution of a deposition process and makes it possible to optimize a possible "anti-deposition" treatment.

Another important aspect of the process according to the invention relates to the heat gradients within the target. In a stationary aero-thermal regime, the target receives from the gas beam, through the impact zone, an intense heat flow which it entirely restitutes to the environment from all the points of its surface. Because of this intense thermal loss which takes place not only by radiation and convection but also by conduction (when there is a thermal bridge between the target and the external environment), there exists a three-dimensional temperature field. In particular, along the exposed side of the target, the temperature decreases radially by radiation and convection from the center of the impact zone (where its value is Ti). This "superficial gradient" is however limited because the exposed side is surrounded by the incidental gas beam which is at the homogeneous temperature Tg. This gradient can be studied by scanning the exposed side of the target with the thermal camera. In the thickness of the target, the temperature decreases between the exposed side and the opposite one. This "in-depth gradient" is an important parameter of the beam-target interaction, in particular when studying the behavior of internally cooled hot parts that display such a marked gradient. It can be characterized by instrumenting the target with temperature gauges inserted at various depths in the target.

The process according to the invention makes it possible to easily modify this in-depth gradient while playing on the nature of the target support. In fact, if the gas temperature Tg stays constant, if the target is fixed against an insulating panel, its heat loss will be weak and Ti will be close to the gas temperature Tg. If the target is fixed at a single point, the heat loss (by radiation and convection) from its non-exposed side will be stronger and Ti will be notably weaker than Tg. If the target is cooled, for example, by an air stream running on its non-exposed side or if it is fixed against a metallic support (creating a thermal bridge), which can be cooled internally using e.g., a variable air flow, as illustrated on FIG. 1, the heat loss will be then intense and the in-depth gradient will be strong, causing an even lower value of Ti.

Within the framework of the invention, it is also possible to expose the target to temperature variations or "excursions." One can impose more or less fast and large rises or drops of temperature. For example, in order to create a positive thermal shock (increase of Ti), one can: (i) reduce the distance Δ; (ii) increase the gas temperature Tg, in particular by increasing the fuel/oxidizer ratio or by actuating the secondary fuel feed or by partially replacing oxygen by nitrogen protoxide which strongly increases Tg); or (iii) reduce the cooling air flow of the metallic support if such a cooled support is used. In order to create a drop or a quench of Ti, one can: (i) simply divert the beam from the target; (ii) increase the distance Δ; (iii) reduce Tg (for example by reducing the fuel/oxidizer ratio or by injecting a diluent or water); or (iv) increase the cooling air flow of the metallic support if such a cooled support is used.

According to another aspect of the invention, such temperature excursions, documented by the thermometric device, make it possible to simulate thermal transients that are likely to occur during the operation of thermal equipment and can be isolated or periodic events. One will note that the very fast response and the very low thermal inertia of the device according to the invention are particularly well adapted to simulate any type of thermal variation even very fast and intense, such as those encountered in the gas turbines and jet engines, in case for example of loss of flame or, in contrary, of "overfiring" events caused for example by an excessive fuel injection.

In addition, one can permanently visually examine the probes during the test and observe the growth of the deposit or its scaling either in stationary test conditions, or during a thermal shock or during the cooling consecutive to test end.

The duration of the collision can range between a few minutes (for example, for the purpose of screening tests) and several hours (for example, for the purpose of a corrosion study). The target is weighed before and after the test and the deposition rate is calculated as its weight gain divided by the test duration. A weight loss indicates on the contrary an erosion effect. The probe can then be subjected, after visual examination, to a complete series of conventional, physical/chemical, and metallographic analyses that can be destructive or non-destructive. Its surface can be examined by optical and Scanning Electron Microscopy (SEM) equipped with microanalysis (EDS), to determine, according to the case, the morphology of the deposit, the erosion or corrosion aspects, or the metallurgical phase changes. X Ray Diffraction (XRD) analysis can be performed either directly on the surface probe or on the scraped deposit, in order to determine the crystallographic phases. The scraped deposit can also be subject to a chemical analysis (anions, cations; carbon; sulfur, phosphorus, etc.).

Finally the process and device according to the invention make it possible to carry out corrosion tests in two steps. In a first stage, using the device, one forms a particles deposit on the target, under well-defined conditions of collision. In a second phase, one exposes the target in an oven or a thermobalance under controlled conditions of temperature and atmosphere, and one monitors the progress of corrosion, with the possibility of making any wished analysis at the end of this exposure.

In summary, the process according to the invention makes it possible to accurately reproduce and study in detail the collisions between a target and a beam of gas and particles at high temperature and high speed with the purpose, in particular, of characterizing the physical/chemical interactions between this beam and the target material. It offers considerable advantages as compared with the state of the art, advantages that result in particular from the possibility of exploring extremely wide ranges of collision conditions, working in stationary or variable aero thermal regimes, fixed or variable geometry configurations, and the possibility of conducting accelerated tests, with the following strong assets: excellent reproducibility; the ability to reproduce any type of gas chemistry, i.e., any type of composition of the carrier gas with limited gas consumption; the ability to reproduce any type of particle chemistry with limited consumption of precursors; the absence of parasitic "memory effects;" the ability to adjust either the gas temperature Tg or the skin temperature Ti of the target; the possibility of imposing sudden rises or falls of temperature (overheating or quench) thanks to the low inertia of the device; and the possibility of varying the incidence angle of the gas beam onto the target.

The present invention will be described in more details using the following examples, to which it is however not limited.

Example 1

Interaction at normal incidence ($\theta=0°$) between a metallic target and a stream of combustion gas and magnesium-vanadium ash, with a skin temperature of 850° C. and a gas speed of 350 m/s.

The objective is to generate and characterize the collision between a gas beam carrying particles of magnesium oxide and magnesium orthovanadate and a flat metal target. The conditions to be simulated are the following: one must have, at the point of impact a skin temperature of the target (Ti) equal to 850° C., a gas speed (Vg) of 350 m/s, and the following mass fluxes of the Mg and V hetero-elements: flux of vanadium: $F_V=7.39 \ 10^{-3}$ kg s$^{-1}$ m$^2$ of V; flux of magnesium $F_{Mg}=2.22 \ 10^{-2}$ kg s$^{-1}$ m$^2$ of Mg.

It will be noticed that this flux of particles is characterized by the fact that the mass ratio Mg/V is equal to 3. The supersonic burner used is a "HVOF" gun operating on liquid fuel and having a net energy of 60 kW. The gas gun and the outlet orifice have a section of 10 mm. The test target is a rectangular plate (75 mm×30 mm×4 mm) machined in NiCr19Fe19Nb5Mo3 alloy (sold under the name Inconel®718 by the company Special Metal Corporation), which has been polished with SiC grain of grade 120 (Ra: 3.0 µm) and which is fixed against a flat, uncooled metal support.

It is first necessary to experimentally determine the parameters of the burner to be adjusted, namely the molar fluxes of fuel and of the oxidizer-diluents, in order to adjust Ti and Vg. Then, on the basis of determined fuel flow, one will calculate the molar fractions $X_V$ and $X_{Mg}$ to be introduced into the fuel to generate the wanted fluxes of the hetero-elements Mg and V, i.e., $F_V$ and $F_{Mg}$. The fuel used is a kerosene quality that contains 14.28% hydrogen and is virtually free from sulfur. Its density is 830 kg/m3. Its "standardized molar formula" (i.e., expressed on the basis of one carbon atom per molecule) is $C_1H_2$, and its molar mass is 14.03 g/mol. The burner is initially lit with this fuel (not yet doped), and the flame is adjusted with the following parameters (primary feeding interface): kerosene 2.65 g/s (0.189 mol/s); oxygen 7.87 Nl/s (0.351 mol/s); air 13.83 Nl/s (0.617 mol/s). Under these conditions, taking into account the composition of the air (20.9% $O_2$+79.1% $N_2$), the combustion reaction of a "standardized mole" of kerosene can be written:

$$CH_2+1.857\ O_2+3.264(0.209\ O_2+0.791\ N_2) \rightarrow CO_2+H_2O+1.039\ O_2+2.582\ N_2$$

Each "standardized mole" of kerosene thus generates 5.621 moles of combustion gases. The combustion gas output of the burner is thus: 0.189*5.621=1.062 mol/s.

As indicated in the description, to avoid having the surface of the test target deteriorated as a consequence of its exposure to the hot gas stream during the adjustment of Ti and Vg, one prefers to substitute to it, during these adjustment operations, an auxiliary target, identical to the test target, this operational precaution not being however essential for the implementation of the invention. The combustion gas beam is directed in a horizontal direction, and using a thermal camera (with an emissivity data taken equal to 0.8), one measures at several points of the beam axis the skin temperature Ti of the auxiliary target, directed vertically and normally to the beam ($\theta=0$), so that the beam interferes in its center. One so determines that it is necessary to place the auxiliary target at the distance $\Delta=0.175$ m from the burner outlet orifice in order Ti is equal to 850° C. At this point, the area ($\sigma$) of the impact zone on the auxiliary target is 5.6 cm$^2$ or 0.00056 m$^2$. It will be noted that the predictive formula (2) gives also $\sigma$=0.00056 m$^2$ (with $\alpha$=5.5°).

The gas temperature Tg at the same point, measured using the "black body radiator" and the thermal camera is equal to 1153° C. The gas speed at the impact point, given by equation (3), is $V_g$=(1.062*0.0224/0.00056) (273+1153)/273=222 m/s. To reach the speed of 350 m/s, as required, one multiplies, on the basis of the same equation (3), the flows of kerosene, oxygen, and air by the factor 350/222=1.577, which keeps unchanged the temperature field within the beam as well as at the point located at the distance $\Delta$ from the burner. The adjustment of the burner operation thus leads to the following flows: kerosene 0.189*1.577=0.298 mol/s; oxygen 0.351*1.577=0.553 mol/s; air 0.618*1.577=0.975 mol/s. The molar flow of combustion gas which is equal to 1.062*1.577=1.675 mol/s, thus makes it possible to reach the speed of 350 m/s at the point of the beam located at $\Delta$=0.175 m.

One can now determine the mass fractions of vanadium and magnesium to be incorporated into the kerosene, which are given by equation (12):

$X_V^{mass}=F_V\sigma/(Q_fM_f)$=7.39 $10^{-3}$*0.00056/(0.265*0.01403)=1.111*10$^{-3}$ kg/kg or 1.114 g of vanadium per kg of fuel.

$X_{Mg}^{mass}=F_{Mg}\sigma/(Q_fM_f)$=2.22 $10^{-2}$*0.00056/(0.265*0.01403)=3.334*10$^{-3}$ kg/kg or 3,351 g of magnesium per kg fuel.

As precursors of the particles, one takes the following oil soluble hetero-molecules: for Mg, magnesium carboxylate (concentration 28.5% Mg in mass); for V, vanadium naphthenate (concentration 3.0% V in mass).

Taking into account these contents Mg and V, prepare the doped fuel, one will thus dissolve, per kg of pure kerosene: 11.73 g of carboxylate of magnesium and 37.67 g of vanadium naphthenate.

The doped fuel having thus been prepared, one replaces in the "device" the undoped fuel by the doped fuel by keeping the set of combustion conditions, and one replaces the auxiliary target by the test target, in the same position A and with the same orientation.

The collision between the beam and the target lasts 34 minutes, during which the skin temperature Ti of the target, which is monitored using the thermal camera, gradually increases from 802 to 967° C. After 34 minutes, the beam is diverted from the test target and the burner is turned off. The weight gain of the probe is 0.86 g, indicating a speed of deposition of 1.52 g/h. The area of the impact zone is 5.7 cm². The analysis by X Rays Diffraction shows the presence of MgO, MgSO4, and Mg3(VO4)2 (magnesium orthovanadate). The deposit obtained forms a monolithic, compact, adherent disc, free from crack, whose thickness is about 1 mm in its center.

A repeat of this test, with identical conditions, gives a speed of deposition of 1.56 g/h, which is an indication of good repeatability. One can thus take 1.54 g/h as average value of the deposition rate under these experimental conditions.

From a practical standpoint, this test is intended to simulate the interaction, within a gas turbine, between a combustion gas stream that transports ash particles made of MgO and $Mg_3V_2O_8$ and impinges, at the 350 m/s speed, the first stage bucket (having a total cross-section of 2.1 m²). This turbine burns 2.8 kg/s of a fuel contaminated by 55.4 vanadium mg/kg and inhibited with magnesium, on the basis of a mass ratio Mg/V equal to 3, that is to say 166.2 mg/kg of magnesium. The mass fluxes of both hetero-elements in the turbine are thus:

$$2.8*55.4 \; 10^{-6}/2.1 = 7.39 \; 10^{-5} \; kg \; s^{-1} \; m^{-2} \text{ for vanadium;}$$
and
$$3*7.38 \; 10^{-5} = 2.22 \; 10^{-4} \; kg \; s^{-1} \; m^{-2} \text{ for magnesium.}$$

Since the fluxes of V and Mg created in the device have been taken equal respectively to $7.39 \; 10^{-3} \; kg \; s^{-1} \; m^2$ and $2.22 \; 10^{-2} \; kg \; s^{-1} \; m^2$ of Mg, the example which has just been described constitutes a severing, by a factor 100 of the situation that prevails in the gas turbine.

Example 2

Interaction, in dynamic conditions, between a test target and a stream of combustion gas and magnesium-vanadium ash.

In this second experiment, the burner is attached to the arm of a remotely controlled multi-axis robot that is able to change within a few seconds the distance Δ between the burner and the target without stopping the collision and modifying the angle of incidence. This experiment which lasts in all 33 minutes comprises two phases, the first of which lasts 9 minutes and reproduces exactly the conditions of experiment 1. At the beginning of this first phase (t=0 minutes), the temperature of the gas beam Tg, measured at the distance Δ=0.175 m from the burner, is 1,155° C., and the corresponding temperature Ti of the target is 805° C. At the end of this phase, at t=9 minutes, the value of Ti has gradually increased from 805 to 849° C. At this moment, one reduces using the robot, in 3 seconds approximately, the distance Δ which passes thus from 0.175 m to 0.15 m and is maintained at this value for 24 minutes, i.e., until the end of the test. At the beginning of this second phase, Ti rises quickly due to the decrease of Δ, passing from 849 to 975° C. in 2 minutes approximately, then continues to grow more slowly. At t=33 minutes (end of the test), the value of Ti is of 1,047° C., and the total weight gain between t=0 minutes and t=33 minutes is 1.35 g which corresponds to a speed of deposition of ashes of 2.45 g/h (average value over the entire duration of test). Experiment 1 having shown that the speed of deposition is repeatable at constant conditions, one can, by taking 1.54 g/h as speed of deposition for the 1st phase, calculate the speed of deposition which prevailed in the 2nd phase, say: (2.45*33−1.54*9)/24=2.79 g/h; i.e., a value 1.8 times higher than in phase 1.

This example illustrates the ability of the system to perform quick temperature variations. From a practical standpoint, it shows the critical effect of the gas temperature on the deposition rate.

Example 3

Interaction between a test target and a stream of combustion gas and magnesium-vanadium ash, under conditions identical to that of example 1 but in the presence of sodium and $SO_2$ in the combustion product.

This time, one wants to generate and characterize, with the same device, the collision between a gas beam which transports particles not only of MgO and $Mg_3V_2O_8$ but also of $Na_2SO_4$ and which moreover contains $SO_2$. The conditions to be simulated are identical to those of example 1, except for the following parameters: the molar sodium flux is selected equal to 30% of the molar vanadium flow which corresponds to an (Na/V) ratio of 0.3 in mole and 0.135 in mass; that is to say, $F_{Na}=9.98 \; 10^{-4} \; kg \; s^{-1} \; m^{-2}$ Na; the molar fraction of $SO_2$ in the combustion gas is not zero but is $Y_{SO2}=1.60 \; 10^{-3}$ mole of sulfur per mole of gas, that is to say, 1,600 ppm in mole (or in volume).

By injecting in the burner the same fluxes of pure fuel and oxidizer-diluent as in example 1, one obtains experimentally, at the distance Δ=17.5 cm from the burner, values of Ti and Tg close to those of example 1. That is to say, Ti=848° C. and Tg: 1149° C., which is acceptable, taking into account uncertainties inherent in this operation.

To prepare the doped fuel, one has to incorporate in the pure kerosene, in addition to the magnesium and vanadium concentrations calculated in the preceding example, a molar fraction of sulfur given by equation (13) where the flows of fuel and gas are the same as in example 1 ($Q_f=0.298$ mol/s and $Q_g=1.675$ mol/s), that is to say:

$$X_S^{mass}=(31.19/M_f)Y_{SO2}(Q_g/Q_f)=0.02 \text{ kg of sulfur per kg fuel (say 2\% S).}$$

A mass fraction of sodium $X_{Na}^{mass}$ equal to $(0.135 \; X_V^{mass})$, say:

$$X_{Na}^{mass}=0.135*1.114 \; 10^{-3}=1.504 \; 10^{-4} \text{ kg Na/kg fuel.}$$

The hetero-molecule selected as a precursor for sulfur is diethyl sulfide, of formula $(C_2H_5)_2S$, molar mass 90.2 g/mol and containing 35.54% of S. The hetero-molecule selected as a precursor for sodium is sodium dodecylbenzenesulfonate of formula $NaC_{18}H_{29}SO_3$, molar mass 348.5 g/mol and containing 6.58% of Na. Consequently, one will introduce, per kg of pure kerosene, the following quantities of precursors: 11.73 g of magnesium carboxylate (value identical to that of example 1); 37.67 g of vanadium naphtenate (value identical to that of example 1); 0.02/0.3554=0.05627 kg or 56.27 g of diethyl sulfide; and 1.504 10−4/0.0658=0.00229 kg or 2.29 g of sodium dodecylbenzenesulfonate.

It will be noted that the sulfur contribution of sodium dodecylbenzenesulfonate is negligible. One replaces in the "device" the undoped fuel by the fuel so doped while keeping the same combustion conditions, and the auxiliary target is replaced by the test target placed in the same position A and in the same orientation. The collision between the beam and the target lasts 33 minutes. During the collision, one observes on the test target a progressive and monotonic increase in temperature and a growth of the deposit. The final deposit is also thick, compact, exempt of cracks, and even more adherent than in example 1. The weight gain is this time 1.12 g, which corresponds to a deposition rate of 2.04 g/h, that is to say an increase by approximately 33% as compared to example No 1. The X Ray Diffraction patterns show the same phases as in example 1. Phase $Na_2SO_4$ is not detected there. However, the $Na_2SO_4$ phase is identified by EDS, which evidences the presence of amorphous or very little crystallized sodium sulfate (vitreous particles).

The same test is reproduced but over a longer duration (60 minutes). One observes visually, on the test target, a monotonic growth of the deposit which takes the shape of a flattened cone whose axis is perpendicular to the center of the impact zone. After 60 minutes, the deposition rate is 2.16 g/hour, say an increase by 40% compared to example 1 (in which sulfur and sodium were absent).

From a practical standpoint, this test simulates, in controlled conditions, the collision between a stream of gas containing $SO_2$ and transporting particles of $Mg_3V_2O_8$, MgO, and Na2SO4 and a gas turbine row. This turbine burns 2.8 kg/s of a fuel contaminated not only by vanadium but also by sulfur and sodium (with a mass ratio Na/V of 0.135), the corrosiveness of vanadium being inhibited by magnesium which is added to the fuel in the mass ratio Mg/V=3 in mass. From a quantitative standpoint, this fuel contains 2% sulfur, 55.4 mg/kg vanadium, 166.3 mg/kg magnesium, and 7.5 mg/kg sodium.

Examples 1 and 3 show that the presence of $Na_2SO_4$ and $SO_2$ in the combustion gas increases the deposition rate of magnesium-vanadium ash. Sodium sulfate (melting point 884° C.) travels in the molten state in the combustion gas which, in the two experiments, happens to hit the target at approximately 1,150° C.

Example 4

Test identical to the test of example 3 but with a cooled support target.

In this test, the conditions are identical to those of example 3, but the metallic support is cooled internally by an air stream, as illustrated in FIG. 1.

One observes, at the beginning of the test, a fall of 44° C. of the temperature of skin Ti as compared to the example 3 (849 against 805° C.). At the end of the 60 minutes of collision, the speed of deposition is 1.10 g/h, corresponding to a reduction by 29% as compared to the uncooled conditions. This example illustrates the effect of cooling of the target on the deposition rate.

Example 5

Interaction between a metallic target and a stream of combustion gas and ash containing nickel and vanadium, with a normal incidence (θ=) 0°, a temperature of 850° C., and a gas speed of 350 m/s at the impact point.

The objective is now to generate and characterize the collision between a test target and a gas beam containing particles of nickel oxide and nickel orthovanadate. The conditions to be simulated are identical to those of example 3, except for certain hetero-elements-precursors and the composition of the fuel. The mass flux of magnesium is this time zero, whereas the mass flux of nickel "$F_{Ni}$" is taken equal to $1.44\ 10^{-2}$ kg s$^{-1}$ m$^2$ of V, that is to say 1.95 times that of vanadium. The mass fluxes of the hetero-elements V, Na, and the molar fraction of $SO_2$ are identical to those taken in example 2, that is to say the flux of vanadium is $7.39\ 10^{-3}$ kg s$^{-1}$ m$^2$, the flux of sodium is $9.98\ 10^{-4}$ kg s$^{-1}$ m$^2$, and the fraction of $SO_2$ in combustion gases ($Y_{SO2}$) is $1.610^{-3}$ mole/mole.

The mass fraction of vanadium to be introduced in the kerosene is identical to those of examples 1 to 3, that is to say $X_V^{mass}=1.111\ 10^{-3}$ kg/kg (1.111 g of vanadium per kg of fuel).

The mass fraction of nickel to be introduced into the kerosene results from equation (8):

$$X_{Ni}^{mass}=F_{Ni}\sigma/(Q_fM_f)=1.44\ 10^{-2}*0.00056/(0.298*0.01403)=1.929\ 10^{-3}\text{ kg/kg or 1.929 g of nickel per kg fuel.}$$

The hetero-molecule containing nickel is nickel acetylacetonate containing 22.1% in nickel mass. In order to facilitate the dissolution of this compound in the fuel, the fuel composition (in volume percentages) is modified in the following manner: 7.5% of acetylacetone which is used to dissolve the nickel acetylacetonate (a slow process); 10% of "carbitol" and 10% of isopropanol which are mixed with the acetylacetone to accelerate this dissolution; 10% of isopropanol; 72.5% of kerosene containing the other three heteroelements (vanadium, sodium and sulfur) and which is added to the preceding mixture.

The final solution is and remains limpid. The doped fuel thus contains nickel acetylacetonate at a concentration of 1.929/0.221=8.729 g/kg; vanadium naphthenate at a concentration of 37.67 g/kg; diethyl sulfide of formula $(C_2H_5)_2S$, at a concentration of 56.27 g/kg (sulfur 2% in mass); and sodium dodecylbenzenesulfonate ($NaC_{18}H_{29}SO_3$) at a concentration of 2.29 g/kg.

The "undoped fuel" also has the composition 7.5% of acetylacetone, 10% of carbitol, 10% of isopropanol, and 72.5% of kerosene.

The oxidizer-diluent is identical, in flow and composition, to that of examples 1 and 3, and the "undoped fuel-doped fuel" sequence is the same, with the use of an auxiliary target during the adjustments of Ti and Vg. It is observed that, as the acetylyacetonate, the carbitol, and the isopropanol have heating values weaker than that of kerosene, the gas temperature is slightly lower and that it is necessary to bring the target slightly closer to the burner (Δ=17.0 cm) to obtain the same temperature of 850° C., which does not change the surface of the zone of impact (5.6 cm$^2$).

It would have also been possible to increase the fuel flow to restore the value of the Tg temperature of examples 1 and 2 at the distance Δ=17.5 cm.

The gas temperature Tg at the point Δ=17.0 cm, measured using the "black body radiator" and the thermal camera is this time 1155° C.

The collision between the test target and the beam lasts this time only 5 minutes. The weight gain is 0.055 g. A DRX analysis of the deposit shows the presence of only $Ni_3V_2O_8$ and a small quantity of NiO.

The same test is repeated but over a longer duration (35 minutes), during which the recording of the temperature at the impact point shows, after 22 minutes, a series of sharp drops followed by slow increases. At the same time, it is observed visually that the ash undergoes a process of cracking and scaling. One obtains, after 35 minutes, a deposition rate of 0.13 g/h, a value 12.3 times lower than that observed, in equivalent conditions, in the case magnesium-vanadium ash (example 2).

From a practical standpoint, this test simulates, in controlled conditions, the collision between a gas beam containing $SO_2$ and transporting particles of $Ni_3V_2O_8$, NiO, and $Na_2SO_4$ and a row of gas turbine buckets. This turbine burns 2.8 kg/s of a fuel contaminated not only with vanadium but also with sulfur (2%) and sodium (with a mass ratio Na/V of 0.135), the corrosiveness of vanadium being inhibited this time by nickel added to fuel in the mass ratio Ni/V of 2.25 (or atomic ratio Ni/V of 1.95). This fuel contains 2% of sulfur (identical to example 2); 55.4 mg/kg of vanadium (identical to example 2); 195.3 mg/kg of nickel; and 7.5 mg/kg of sodium (identical to example 2).

The results of this test are explained by the fact that nickel orthovanadate, which is much more refractory than that of magnesium, sticks much less to the wall of the test target and has thermal properties preventing its adhesion to the substrate.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A process to create a collision in controlled conditions between a stream of gas and particles and a target, characterized in that the collision is implemented according to desired values, defined at the impact point between the stream and the target, of the gas temperature or the temperature of the target and the gas speed, and the process comprises:
   a. generating a stream of gas and particles, of given composition, in the form of a unidirectional beam, using a supersonic burner comprising a combustion chamber and a gas gun, the combustion chamber being fed with a set of fluids comprising a set of gases comprising an oxidizer, and a liquid fuel having a composition providing after combustion the given composition of gas and particles, the liquid fuel including, as precursors of particles, hetero-molecules either in oil soluble form or in water soluble, emulsified form, and, as precursors of gas, hetero-elements selected among S, P, and the halogens;
   b. generating a collision between the beam and the target;
   c. adjusting fuel flow, the flow of each gas, and the adjustment of the distance between the burner and the target, so as to obtain at the impact point the desired values of the following parameters: (i) the gas temperature or the temperature of the target, and (ii) the gas speed; and
   d. monitoring the temperature of the target at the impact point in the course of time in order to characterize the nature of the particle-target interaction, wherein a constant temperature during the test characterizes an absence of ash deposition, an increase in the temperature characterizes an ash deposition process, and an temperature evolution showing an increase interrupted with drops characterizes deposition of particles interrupted by cracking or scaling processes.

2. The process according to claim 1, characterized in that the set of gas comprises air or one or more diluent gases chosen among nitrogen, carbon dioxide, and rare gases.

3. The process according to claim 1, characterized in that the set of gases comprises one or more gases chosen among sulfur dioxide and the halogens.

4. The process according to claim 1, characterized in that the burner is moreover fed, downstream from the combustion chamber, with a compound chosen among a fuel designated as secondary fuel, liquid water, and particles designated as secondary particles.

5. The process according to claim 1, characterized in that one creates, during the collision, a relative movement between the target and the beam, the movement being a translation movement, a rotation movement, or a combination of a translation and a rotation.

6. The process according to claim 1, characterized in that it comprises the exposure of the target to a collision in controlled conditions with a flow of secondary particles.

7. Use of a process according to claim 1 to simulate and characterize the physical/chemical interactions between the target and the stream of gas and particles.

8. Use of a process according to claim 7 to simulate and characterize a process of erosion, adhesion or corrosion.

* * * * *

UNITED STATES PATENT AND TRADEMARK OFFICE
CERTIFICATE OF CORRECTION

| | | |
|---|---|---|
| PATENT NO. | : 9,046,221 B2 | Page 1 of 1 |
| APPLICATION NO. | : 13/719876 | |
| DATED | : June 2, 2015 | |
| INVENTOR(S) | : Michel Moliere and Christophe Verdy | |

It is certified that error appears in the above-identified patent and that said Letters Patent is hereby corrected as shown below:

In the claims

Claim 1, column 26, line 22, reads "drops characterizes deposition of particles interruptued" should read --drops characterizes a deposition of particles interrupted--

Signed and Sealed this
Seventeenth Day of May, 2016

Michelle K. Lee
*Director of the United States Patent and Trademark Office*